(12) United States Patent
Falci

(10) Patent No.: US 11,596,596 B2
(45) Date of Patent: Mar. 7, 2023

(54) TREATING NEUROPATHIC PAIN IN SPINAL CORD INJURED INDIVIDUALS

(71) Applicant: CNS BIOSCIENCES, INC., Englewood, CO (US)

(72) Inventor: Scott P. Falci, Morrison, CO (US)

(73) Assignee: CNS BIOSCIENCES, INC., Englewood, CO (US)

( * ) Notice: Subject to any disclaimer, the term of this patent is extended or adjusted under 35 U.S.C. 154(b) by 0 days.

(21) Appl. No.: 16/341,855

(22) PCT Filed: Oct. 16, 2017

(86) PCT No.: PCT/US2017/056745
§ 371 (c)(1),
(2) Date: Apr. 12, 2019

(87) PCT Pub. No.: WO2018/071893
PCT Pub. Date: Apr. 19, 2018

(65) Prior Publication Data
US 2019/0321659 A1    Oct. 24, 2019

Related U.S. Application Data

(60) Provisional application No. 62/408,490, filed on Oct. 14, 2016.

(51) Int. Cl.
| | | |
|---|---|---|
| *A61K 31/4015* | (2006.01) | |
| *A61K 9/19* | (2006.01) | |
| *A61K 9/00* | (2006.01) | |
| *A61P 25/00* | (2006.01) | |
| *A61P 29/00* | (2006.01) | |

(52) U.S. Cl.
CPC ............ *A61K 9/0019* (2013.01); *A61P 25/00* (2018.01); *A61P 29/00* (2018.01); *A61K 9/0085* (2013.01); *A61K 31/4015* (2013.01)

(58) Field of Classification Search
CPC ................................................. A61K 31/4015
USPC ............................................................ 514/424
See application file for complete search history.

(56) References Cited

U.S. PATENT DOCUMENTS

| | | | | |
|---|---|---|---|---|
| 8,722,668 B2 * | 5/2014 | Hochman | .............. | A61K 31/00 514/223.2 |
| 2010/0125096 A1 * | 5/2010 | Farina | ..................... | A61K 31/40 514/393 |
| 2011/0178177 A1 | 7/2011 | Wolicki et al. | | |

FOREIGN PATENT DOCUMENTS

| | | |
|---|---|---|
| WO | WO 2001/039779 A1 | 6/2001 |
| WO | WO 2015/110435 A1 | 7/2015 |

OTHER PUBLICATIONS

Finnerup et al. "Levetiracetam in spinal cord injury pain: a randomized controlled trial," Spinal Cord, 2009, vol. 47, pp. 861-867 (Year: 2009).*
Siddal et al. "The efficacy of intracthecal morphine and clonidine in the treatment of pain after spinal cord injury," Anesth. Analg. 2000, vol. 91, pp. 1493-1498. (Year: 2000).*
Hook et al.; "Intrathecal Morphine Attenuates Recovery of Function after a Spinal Cord injury"; Journal of Neurotrauma; May 2009; 12 pages.
Drysdale et al.; "Phantom sensations in people with complete spinal cord lesions: A grounded theory perspective" Disability and Rehabilitation, 2009; 31(4); pp. 267-276.
Siddall et al.; "Classification of pain following spinal cord Injury"; Spinal Cord (1997) 35: pp. 69-75.
Falci et al.; "Dorsal root entry zone microcoagulation for spinal cord injury-related central pain: operative intramedullary electrophysiological guidance and clinical outcome": Journal of Neurosurgery; Sep. 2002; 9 pages.

* cited by examiner

*Primary Examiner* — Shengjun Wang
(74) *Attorney, Agent, or Firm* — BakerHostetler

(57) ABSTRACT

Methods of treating neuropathic pain in spinal cord injured individuals by administering levetiracetam or brivaracetam are described.

2 Claims, 10 Drawing Sheets

TREATING NEUROPATHIC PAIN IN SPINAL CORD INJURED INDIVIDUALS

PRIORITY

The patent application claims priority to U.S. Provisional Patent Application No. 62/408,490 filed on Oct. 14, 2016, the contents of which are incorporated herein by reference in their entirety.

FIELD

Disclosed herein are methods of treating neuropathic pain in spinal cord injured individuals by administering levetiracetam or brivaracetam.

BACKGROUND

Spinal cord injury (SCI) frequently results in severe or disabling pain. Individuals with a SCI suffer anywhere from between 20 and 77% incidence of some level of severe or disabling chronic pain. Davis et al., Clin Orthop 112:76-80 (1975); Richards et al., Pain 8:355-366 (1980); Siddall et al., Spinal Cord 39:63-73 (2001); Stormer et al., Spinal Cord 446-455 (1997); Woolsey, J Am Paraplegia 9:39-41 (1986). Patients suffering from at least some level of severe or disabling chronic pain show reduced rehabilitation potential and tend to have a significant overall reduction in quality of life.

Central pain has proven notoriously difficult to treat, often proving recalcitrant to modern medical and surgical pain treatment procedures. Surgical treatment of specific dorsal root entry zone(s) (DREZ(s)) of the spinal cord are of particular interest. Surgical treatment of a central pain generating DREZ at the level of an injury is believed to disrupt the neural, i.e., electrical, communication and/or generation of aberrant pain signals that result from the injury. Initially, empirical techniques have been used to target DREZ sites for surgical treatment, resulting in modest outcomes for the patient, i.e., DREZ sites at the site of injury targeted for treatment. Friedman et al., J Neurosurg 65:465-469 (1986); Ishijima et al., Appl Neurophysiol 51:2-5, 175-187 (1988); Rath et al., Acta Neurochir, 138:4, 364-369 (1996); Rath et al., Sterotact Funct Neurosurg 68:1-4, Pt 1, 161-167 (1997). One of the more relevant patient studies using this empirical technique suggests that approximately 50% of patients so treated achieve good relief from SCI associated pain. Friedman et al., J Neurosurg. 65:465-469 (1986). In that series, at-level pain, i.e., pain at the immediate vicinity of the injury, responded best (74% "good results") and below-level pain, i.e., pain below the level of injury, responded poorly (20% "good results").

Anti-epileptic drugs are often suggested for treating neuropathic pain. Two of these commercially approved compounds, levetiracetam and brivaracetam, are 2-oxo-pyrrolidin-1-yl bytanamide derivatives that act by binding to synaptic vesicle glycoprotein 2A (SV2A). However, this class of compounds has been disparaged as a method of treating pain in SCI individuals. Finnerup et al., Scandinavian Journal of Pain 1, S1 (2009) S3-S11, described levetiracetam as ineffective in treating pain resulting from spinal cord injury. According to Finnerup et al., "levetiracetam does not relieve neuropathic pain or spasm severity following spinal cord injury." Finnerup et al. further pointed out that the lack of efficacy on the postmastectomy syndrome suggests a lack of interference with mechanisms underlying peripheral postsurgical neuropathic pain as well. Finnerup et al. suggested that it is possible that the pharmacological action of levetiracetam is not involved in neuropathic pain mechanisms and that interference with the SV2A in levetiracetam doses used in humans will have no impact on neuropathic pain.

Levetiracetam has been shown to have no analgesic or other benefit in patients with neuropathic pain following SCI. This suggests that the same would be true for any SV2A-affecting compound, including brivaracetam. (Finnerup et al.).

SUMMARY

Contrary to the general understanding in the field, the disclosure shows that there is a strong correlation between SV2A and SCI neuropathic pain.

In one aspect, the disclosure is directed to methods of treating neuropathic pain in a spinal cord injured individual in need thereof. A 2-oxo-pyrrolidin-1-yl bytanamide derivative is administered to the Individual.

In some aspects, the 2-oxo-pyrrolidin-1-yl bytanamide derivative is levetiracetam ((S)-2-(2-oxopyrrolidin-1-yl)butanamide). In other variations, 2-oxo-pyrrolidin-1-yl bytanamide derivative is brivaracetam (2-(2-oxo-4-propylpyrrolidin-1-yl)butanamide).

In some aspects, the neuropathic pain is perceived by the patient to be below the level of the spinal cord injury. In some aspects, the neuropathic pain is perceived by the patient to be below the neurological level of the spinal cord injury. In some variations, the pain is generated by spinal cord tissue caudal to the level of the spinal cord injury. In some variations, the pain is generated by spinal cord tissue cephalad to the level of the spinal cord injury.

The neuropathic pain drug can be administered below the level of the spinal cord injury. Further, the 2-oxo-pyrrolidin-1-yl bytanamide derivative can be administered intrathecally, below the level of spinal cord injury.

BRIEF DESCRIPTION OF THE DRAWINGS

The following drawings are made to illustrate aspects of the present disclosure, and are not intended to be limiting.

DETAILED DESCRIPTION

Figure 1:
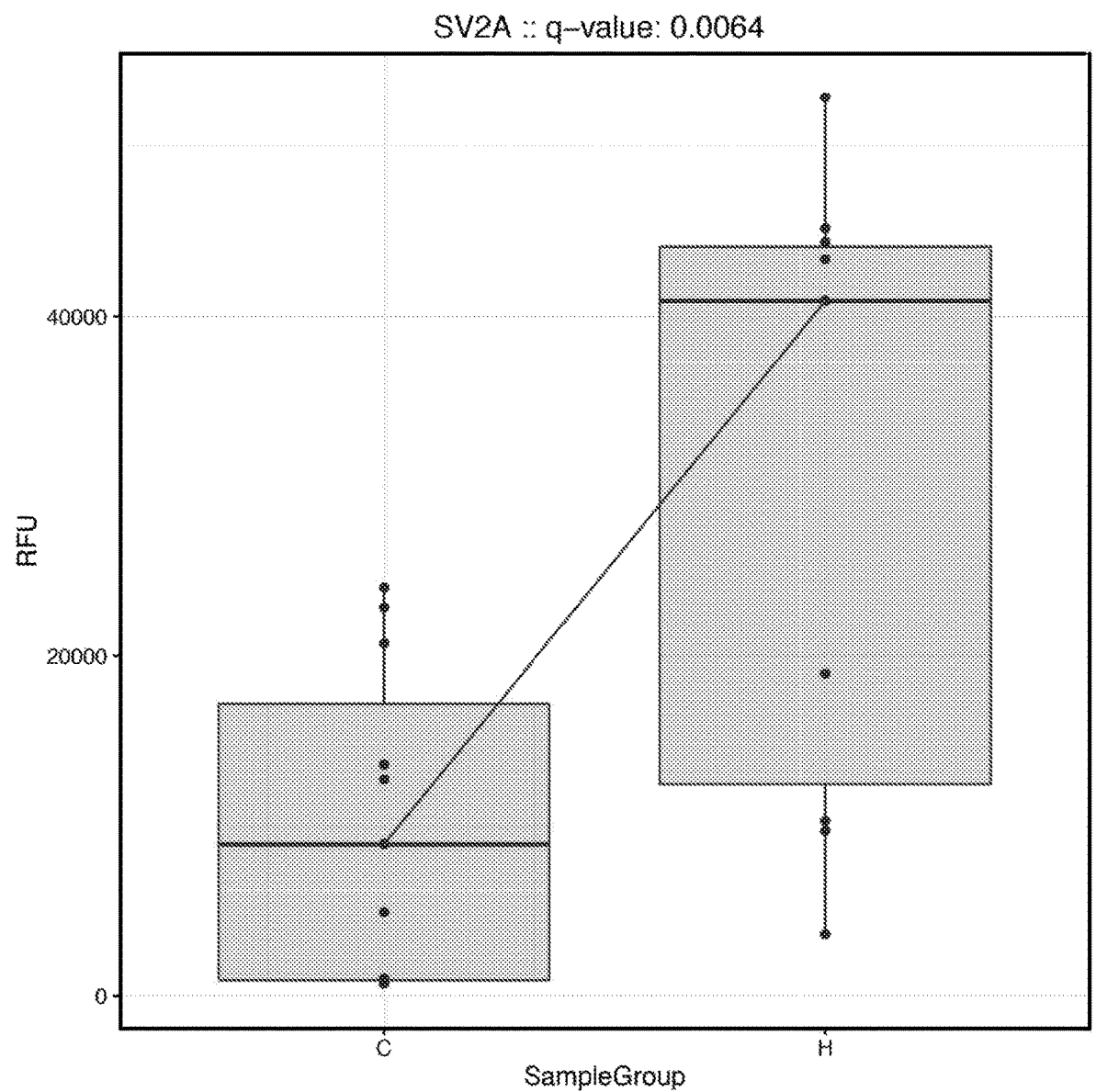
FIG. 1 depicts a box plot representation of SV2A, according an illustrative embodiment.

This disclosure relates to using levetiracetam or brivaracetam to treat neuropathic pain in spinal cord injured individuals. Pain-producing tissues correlating with sympathetically mediated central neuropathic pain in SCI patients were acquired. Comparative analysis of molecular markers between electrically hyperactive pain-producing tissue and electrically normal non-pain producing tissue showed an upregulation of SV2A in the pain-producing tissue implicated in sympathetically mediated central pain. Contrary to the prevailing view, the SV2A is implicated in spinal cord injury neuropathic pain. As such, drugs such as levetiracetam or brivaracetam that act on SV2A can be used to treat SCI pain, including sympathetically medicated central pain perceived below the neurological level the SCI. Pain includes neuropathic, SCI pain, and central pains referring to their central nervous system origin.

Methods of treating (i.e. alleviating, reducing, diminishing or otherwise attenuating) neuropathic pain in a patient in need thereof by administering 2-oxo-pyrrolidin-1-yl bytanamide derivatives such as levetiracetam or brivaracetam are described herein.

Relieving SCI neuropathic pain has become an extremely difficult problem with either pharmacological or surgical treatment. It has generally been believed that generators of SCI pain must come solely from spinal cord regions above (cephalad) the level of SCI or from the brain itself. Extreme surgical measures such as complete spinal cord transection have been performed to eliminate all possible influence of the spinal cord below the level of injury in these severe and pharmacologically refractory pains.

It has now been discovered that spinal cord below (caudal) the level of injury can, in fact, generate below-level SCI neuropathic pain and be its sole source. In particular, eradicating spinal cord regions of hyperactivity below the level of injury within the dorsal grey matter (Rexed layers 1-3) can result in complete pain relief, even if the spinal cord had been completely transected.

Spinal cord pain can be mediated through the sympathetic nervous system. Specifically, hyperactive electrical neuronal signals originating in spinal cord below the level of injury can be routed around the injury site by way of the sympathetic chain to reach brain pain centers. The pain is be perceived as below the neurological level of spinal cord injury, where it should not be perceived. For example, in a complete spinal cord injury at the neurological level of T10, a patient should not feel lower (caudal) pain from the umbilicus. However, the patient can nevertheless perceive pain in these regions. The pain can be generated by tissues located below (caudal to) the level of spinal cord injury or above (cephalad to) the level of spinal cord injury. Such sympathetically mediated spinal cord injury pain is perceived by the patient to be below the neurological level of spinal cord injury (referred to herein as "below-level pain").

Contrary to expectations in the art, SV2A has been discovered to correlate with below-level pain. Specifically, SV2A is markedly upregulated in electrically hyperactive spinal cord tissue caudal to the level of injury and/or cephalad to the level of injury, and eradication of this hyperactive tissue can result in complete pain relief, even if the spinal cord had been completely transected prior. As such, SV2A, with its increase in expression after spinal cord injury, has been identified as a generator of neuropathic pain perceived below the neurological level of spinal cord injury (sympathetically mediated pain).

Contrary to conventional wisdom, levetiracetam and brivaracetam can relieve below-level neuropathic pain (sympathetically mediated pain) with oral, SC, IV, sublingual, intra, or intrathecal administration. Drugs associated with below level pain, including levetiracetam or brivaracetam, can be used to treat pain, including pain perceived as below the neurological level of spinal cord injury.

Definitions

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the disclosure may be administered to a patient and which does not destroy the pharmacological activity thereof and which is non-toxic when administered in doses sufficient to provide a therapeutically effective amount of the compound.

"Pharmaceutical composition" refers to levetiracetam or brivaracetam and at least one pharmaceutically acceptable vehicle with which levetiracetam or brivaracetam is administered to a patient.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, as well as the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

Compounds

Levetiracetam and brivaracetam are antiepileptic medications. Both levetiracetam and brivaracetam are 2-oxo-pyrrolidin-1-yl bytanamide derivatives. Levetiracetam, or (S)-2-(2-oxopyrrolidin-1-yl)butanamide, is a single enantiomer prescribed as a treatment for certain types of seizures. Brivaracetam, or 2-(2-oxo-4-propylpyrrolidin-1-yl)butanamide, is an analog of levetiracetam.

Both levetiracetam and brivaracetam bind to SV2A, a known target of anti-epileptic drugs. Though suggested as drugs that can be used to treat neuropathic pain, levetiracetam has been believed not to have an effect on pain in SCI patients, including pain below the level of the site of injury.

The disclosure is directed to treating pain in spinal cord injured individuals. In some variations, levetiracetam or brivaracetam is administered to an individual to treat neuropathic pain. In additional variations, levetiracetam or brivaracetam is administered to an individual to treat neuropathic pain in a spinal cord injured individual. In further variations, levetiracetam or brivaracetam is administered to treat sympathetically mediated central nervous system pain in a spinal cord injured individual. In still further, the neuropathic pain can be sympathetically mediated. In additional variations, the neuropathic pain is perceived below the neurological level of injury. In additional variations, pain generating spinal cord tissue originates below the level of the location of spinal cord injury.

Pharmaceutical Compositions

Pharmaceutical compositions provided by the disclosure may comprise a therapeutically effective amount of levetiracetam or brivaracetam together with a suitable amount of one or more pharmaceutically acceptable vehicles so as to provide a composition for proper administration to an individual. Suitable pharmaceutical vehicles are described in the art.

In certain embodiments, levetiracetam or brivaracetam may be incorporated into pharmaceutical compositions to be administered intrathecally. Oral compositions may be prepared in a manner known in the pharmaceutical art and comprise levetiracetam or brivaracetam and at least one pharmaceutically acceptable vehicle. Oral pharmaceutical compositions may include a therapeutically effective amount of levetiracetam or brivaracetam and a suitable amount of a pharmaceutically acceptable vehicle, so as to provide an appropriate form for administration to an individual.

Pharmaceutical compositions comprising levetiracetam or brivaracetam may be manufactured by conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of the compounds and one or more pharmaceutically acceptable vehicles into formulations that can be used pharmaceutically. Proper formulation is dependent upon the route of administration chosen. Pharmaceutical compositions provided by the disclosure may take the form of solutions, suspensions, emulsion, tablets, pills, pellets, capsules, capsules containing liquids, powders, suppositories, emulsions, aerosols, sprays, suspensions, or any other form suitable for administration to an individual.

Pharmaceutical compositions are suitable for parenteral administration, including intrathecal injection. The pharmaceutical can be a sterile injectable preparation of levetiracetam or brivaracetam in, for example, a solution which is isotonic with the blood or cerebrospinal fluid of the recipient. Useful formulations also comprise concentrated solutions or solids containing the active ingredient which upon dilution with an appropriate solvent give a solution suitable for parenteral (including intrathecal) administration. The parenteral compositions include aqueous and non-aqueous formulations which may contain conventional adjuvants such as buffers, bacteriostats, sugars, thickening agents and the like. The compositions may be presented in unit dose or multi-dose containers, for example, sealed ampules and vials.

Levetiracetam or brivaracetam may be incorporated into pharmaceutical compositions for administration by any other appropriate route of administration including p.o. (by mouth), IV (intravenously), SC (subcutaneously), IC (intrathecally—spinal fluid), intranasally, and sublingually.

Pharmaceutical compositions provided by the disclosure may be formulated in a unit dosage form. A unit dosage form refers to a physically discrete unit suitable as a unitary dose for individuals undergoing treatment, with each unit containing a predetermined quantity of levetiracetam or brivaracetam calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to an individual at a single point in time or during a time interval.

The amount of a levetiracetam dose can be chosen to any quantity appropriate for a specific treatment. In some variations, the levetiracetam dose can be at least 20 mg, 40 mg, 60 mg, 80 mg, 100 mg, 120 mg, 140 mg, 160 mg, 180 mg, and 200 mg. In some variations, the dose can be less than or equal to 300 mg, 280 mg, 260 mg, 240 mg, 220 mg, 200 mg, 180 mg, 160 mg, 140 mg, 120 mg, and 100 mg.

In some variations, levetiracetam can be administered by intravenous infusion at a daily dose of 1000 mg. The daily dose can be administered as a twice daily 500 mg dose. In some variations, the dose can increase in increments of 1000 mg/day every two weeks to a maximum daily dose of 3000 mg. In some variations, levetiracetam can be administered in 1000 mg once daily doses. In some variations, levetiracetam can be administered in increments of 1000 mg every two weeks to the maximum daily dose of 3000 mg. In some variations, the daily dose of levetiracetam can be administered as an oral solution of 100 mg/ml. In some variations, levetiracetam can be administered as a 250 mg, 500 mg, 750 mg, or 1 gram tablet.

In some variations, levetiracetam can be administered intrathecally, such as with an infusion pump (e.g., the Medtronic Synchromed II Programmable Infusion Pump). Intrathecal administration can has lower dosing than other dosing methods, and can be delivered continuously, as a bolus, or with varying concentration over a period of time. In some variations, the levetiracetam intrathecal dose can be at least 20 micrograms, 40 micrograms, 60 micrograms, 80 micrograms, 100 micrograms, 120 micrograms, 140 micrograms, 160 micrograms, 180 micrograms, and 200 micrograms. In some variations, the dose can be less than or equal to 300 micrograms, 280 micrograms, 260 micrograms, 240 micrograms, 220 micrograms, 200 micrograms, 180 micrograms, 160 micrograms, 140 micrograms, 120 micrograms, and 100 micrograms.

In some variations, the brivaracetam dose can be at least 10 mg, 25 mg, 50 mg, 75 mg, 100 mg, 125 mg, 150 mg, 175 mg, or 200 mg. In some variations, the dose can be less than or equal to 300 mg, 275 mg, 250 mg, 225 mg, 200 mg, 175 mg, 150 mg, 125 mg, or 100 mg. In some variations, brivaracetam can be administered as an oral solution of 100 mg/mL. Such variations can be by any mode of administration, including intravenous and oral administration. Brivaracetam can be administered as 50 mg PO BID initially. Based on individual tolerability and therapeutic responses, the dose can be adjusted down to 25 mg BID (50 mg/day) or up to 100 mg BID (200 mg/day). Alternatively, brivaracetam can be administered by IV injection. Injection can be at the same dosage and same frequency as tablets or oral solution. In some variations, brivaracetam can be administered intravenously at 50 mg/5 mL. In some variations, brivaracetam can be administered by oral tablets at 10 mg, 25 mg, 50 mg, 75 mg, or 100 mg.

In some variations, brivaracetam can be administered intrathecally. As with intrathecal levetiracetam administration, administration can has lower dosing than other dosing methods, and can be delivered continuously, as a bolus, or with varying concentration over a period of time. In some variations, the brivaracetam dose can be at least 10 micrograms, 25 micrograms, 50 micrograms, 75 micrograms, 100 micrograms, 125 micrograms, 150 micrograms, 175 micrograms, or 200 micrograms. In some variations, the dose can be less than or equal to 300 micrograms, 275 micrograms, 250 micrograms, 225 micrograms, 200 micrograms, 175 micrograms, 150 micrograms, 125 micrograms, or 100 micrograms.

An appropriate dose of levetiracetam or brivaracetam or pharmaceutical composition comprising levetiracetam or brivaracetam may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as, for example, humans.

In some variations, brivaracetam or levteracetam can be administered as recommended by FDA guidance.

Brivaracetam can be administered as an intravenous solution at 10 mg/mL, a 10 mg/mL oral solution, or as tablets. For tablet or oral solution administration, the recommended starting dosage is 50 mg twice daily. Based on individual patient tolerability and therapeutic response, the dosage may be adjusted down to 25 mg twice daily (50 mg per day) or up to 100 mg twice daily (200 mg per day). When oral administration is not feasible, the same dosage can be administered by intravenous injection. The dosage of brivaracetam can be altered from the approved dosage.

Levteracetam can be administered orally at 1000 mg daily as an oral immediate release or oral extended release. Levteracetam can be administered by intravenous injection when oral administration is not feasible. The dosage of levteracetam can be altered from the approved dosage.

Either brivaracetam or levteracetam can be administered in varying amounts lower or higher than described herein without departing from the scope of the disclosure.

EXAMPLES

The following examples provide support for aspects of the disclosure. They are not intended to be limiting. To the contrary, the examples can be varied in keeping with the spirit of the disclosure.

Example 1: Tissues from Spinal Cord Injured Individuals

Tissues implicated in spinal cord pain were acquired and fast frozen. Methods of acquiring tissues that that exhibit spinal cord pain are have been described, for example, in U.S. Pat. No. 8,694,107, incorporated herein by reference in its entirety.

Spinal cord tissues producing central pain were acquired surgically. First, the spinal cord tissue implicated in perceived pain was determined by comparing the anatomical location of perceived pain to a somatotopic map of SCI neuropathic pain generating spinal cord tissue. Spinal cord tissue displaying hyperactive electrical signals were then identified in these spinal cord regions by measuring electrical hyperactivity of tissues. Non-electrically hyperactive, non-pain generating DREZ sites, were identified in the same individual. Samples of both the hyperactive, pain generating DREZ SPINAL CORD TISSUE and non-hyperactive, non-pain generating DREZ spinal cord tissue was taken from the individual.

Tissues were obtained surgically exposing the DREZ tissue inclusive of the substantia gelatinosa tissue above (cephalad), below (caudal), and at the level of injury. A recording electrode was inserted approximately 2 mm deep into the dorsal grey matter of the spinal cord, entering at the dorsal root entry zone (DREZ). Recordings of spontaneous electrical activity were recorded for one second.

Recordings were performed bilaterally along the DREZs cephalad and caudal to the level of the injury approximately 1 mm apart. The recordings were analyzed using fast Fourier transform (FFT) root Mean Square analysis and "spindle" analysis (as disclosed in U.S. Patent Publication Nos. 2010/0203022 and 2007/0016264, both of which are incorporated herein by reference) to identify regions of neuroelectrical hyperactivity. The regions recorded correspond to Rexed layers 1, 2, and 3 within the dorsal grey matter.

The recordings were guided by a somatotopic map, and made both cephalad and caudal to the level of injury as well as at the level of the injury until no additional electrical hyperactivity was detected. A small cut in the pia was made and a micro-pituitary rongeur was inserted to remove an approximate 1×1×2 mm piece of dorsal grey matter. The tissue was identified as pain-producing "hyperactive" or non-pain producing "normoelectric" based on the electrical recordings. The tissue was snap-frozen within 10 minutes of excision and stored at −81° C.

Tissue is acquired both from hyperactive (i.e., pain generating) and non-hyperactive (i.e., non-pain generating) DREZ sites to determine the difference in protein expression. Expressed proteins are markers of spinal cord injury pain.

Tissue from hyperactive and non-hyperactive spinal cord was then tested against a 4,000 marker panel, including for SV2A.

Example 2: SV2A Expression

The tissue was extracted using T—Per tissue protein extraction agent (Thermo Scientific) per the manufacturer's recommendation. 200 µL of buffer plus Halt protease inhibitor cocktail (Pierce Part #78430) was added. The tissue was homogenized in a tube on ice with a rotary pestle for 30 seconds until no tissue fragments were visible. The sample was centrifuged at >14,000×g for 10 minutes while at 4° C. The supernatant was filtered through a 0.2 micron filter into a sterile tube or plate while at 0° C. Millipore Multiscreen GV filter plate, 0.22 µm, sterile, Part #MSGV2210 or similar). The amount of total protein was determined using Micro BCA Protein Assay Kit (Thermo Scientific). Aliquots were stored at −81° C.

The tissues were tested by SOMAscan® analysis. SOMAscan tests tissue against a 4,000 protein panel (including SV2A), and a range of concentrations. SOMAscan® and related methods and reagents are described, for example, at U.S. Pat. Nos. 5,843,653; 5,853,984; 5,989,823; 6,261,783; 6,329,145; 6,531,286; 6,670,132; 6,673,553; 6,706,482; 7,709,192; 7,855,054; 7,964,356; 8,975,026 and 8,945,830, which are incorporated by reference in their entirety.

Hyperactive pain producing tissue was compared to non-pain producing tissue. Targets that were upregulated in hyperactive (pain producing) tissue as compared to non-pain producing tissue were identified as pain targets. These pain targets were analyzed for drugs effective against the target.

A box plot representation of SV2A is depicted in FIG. 1. The left box shows the RFU values of SV2A protein expression in the control group of electrically normal non-pain producing spinal cord tissue from a patient with neuropathic pain perceived below the neurological level of SCI. The horizontal line in the control group is the median RFU value of SV2A protein expression of electrically normal non-pain producing spinal cord tissue in the control group. The right box represents the measured RFU values of SV2A protein expression of electrically hyperactive pain-producing spinal cord tissue acquired from the same patient with below-level spinal cord injury neuropathic pain. The horizontal black line in the pain-producing group depicts the median RFU value of SV2A protein expression of electrically hyperactive pain-producing spinal cord tissue acquired from the same patient with below-level spinal cord injury neuropathic pain.

Based on the compared SV2A expression, SV2A shows a 4.6 fold increase in expression in the pain-producing tissue. The ratio of SV2A in hyperactive substantia gelatinosa tissue compared to normo-active substantia gelatinosa tissue was 4.6. The q-value of the RFU analysis was 0.0064.

The hyperactive spinal tissue showed an increase in SV2A concentration over non-hyperactive spinal tissue. Surgical destruction of this hyperactive tissue resulted in complete relief of below-level neuropathic pain. SV2A is therefore a target for treating neuropathic pain in spinal cord injured individuals, particularly those with sympathetically mediated central pain or pain below the level of spinal cord injury.

SV2A expression in pain-producing cord therefore correlates with neuropathic pain. Synaptic vesicle glycoprotein 2A is a ubiquitous synaptic vesicle protein that in humans is encoded by the SV2A gene.

Example 3

Figure 2:
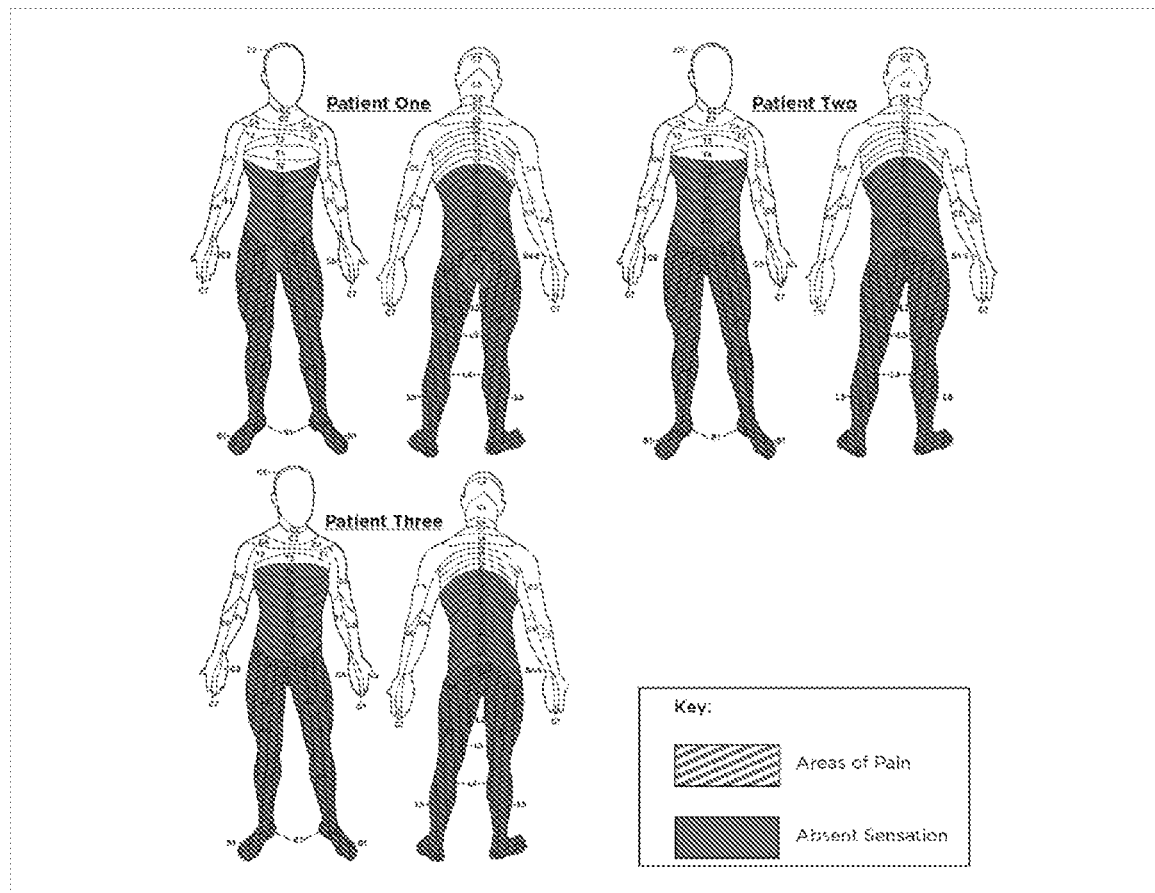
FIG. 2 depicts a preoperative sensory chart and regions of perceived below-level pain, according to an illustrative embodiment.

Three patients were aged 49, 54, and 45 years. All were male. All sustained thoracic spinal cord injuries. All experienced severe below-level neuropathic pain (FIG. 2). Below-level pains were first experienced at 19 years, 2 months, and 2 months post injury, respectively. Time to surgery from onset of significant below-level pain was 2 years, 8 years, and 13 years, respectively. Descriptors characterizing the pains were "sharp", "burning", and "electrical" (Table 1)

TABLE 1

| Patient | Age | ASIA Classification | Years with Severe Pain | Pain Descriptors |
|---|---|---|---|---|
| 1 | 49 | T5 A | 2 | burning |
| 2 | 54 | T4 A | 6 | Burning |
| 3 | 45 | T3 A | 13 | Burning, stabbing, electrical, pins-needles |

Figure 6:
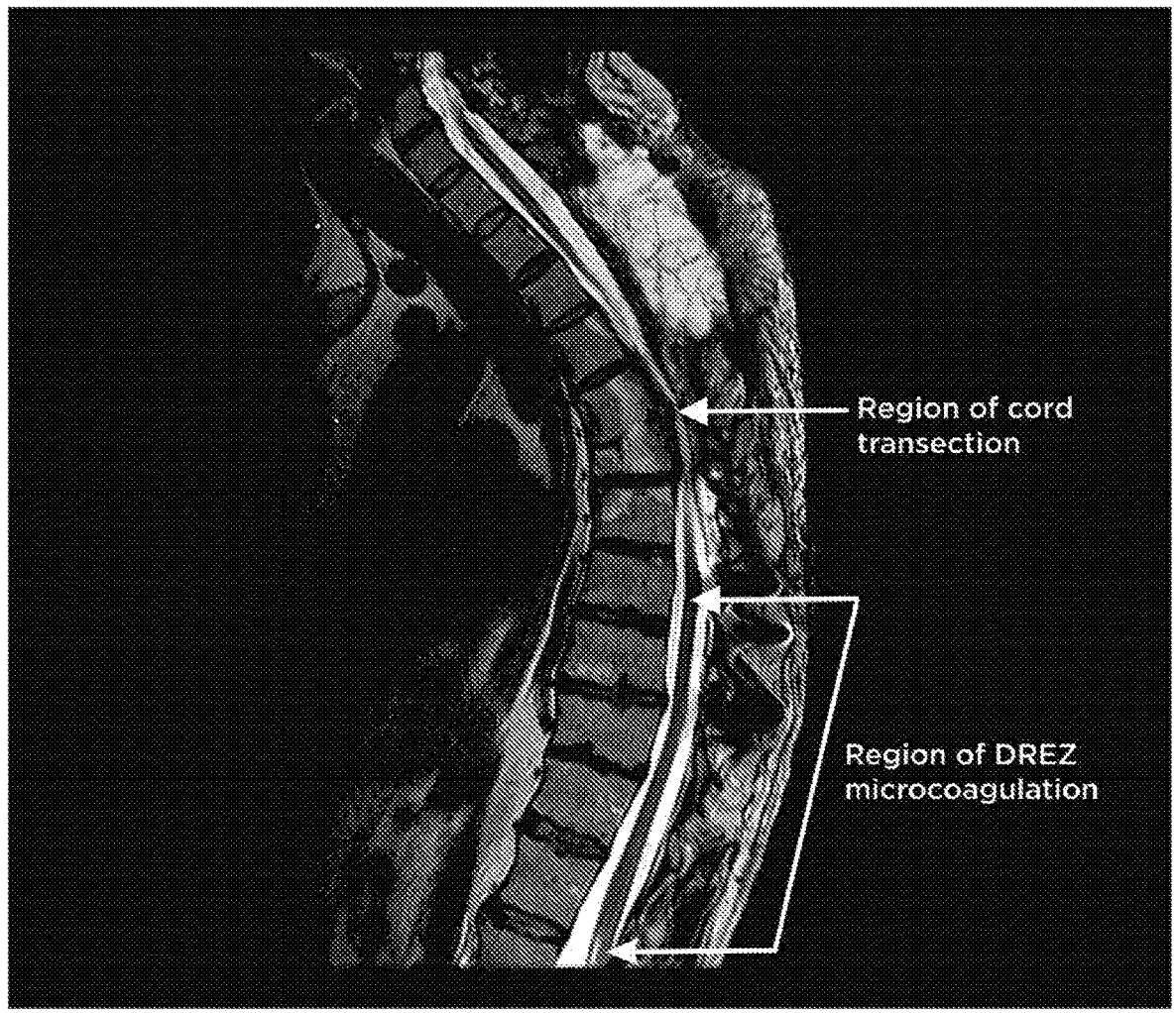
FIG. 6 depicts T2 weighted MRI showing regions of spinal cord transection and regions of DREZ microcoagulation of a patient, according an illustrative embodiment.

All three patients had undergone previous surgery to the spinal cord. One of the three patients had undergone previous spinal cord untethering surgery with expansion duraplasty and cyst shunting, in a failed attempt to alleviate his below-level pain. The other two patients had previously undergone DREZ microcoagulation at and cephalad to the level of injury in an attempt to alleviate SCI at-level and below-level neuropathic pain, achieving complete relief only of at-level pain. No long term below-level pain relief was achieved in any of the three. All three patients were noted to have essentially complete traumatic spinal cord transections at the injury site, visually confirmed during the previous surgeries to the spinal cords described above. During these surgeries, a thin band of avascular scar found at the injury site replacing normal cord tissue, was transected, resulting in visually clear and separate ascending and descending portions of the spinal cord (FIG. 6). Four or more months subsequent to these prior surgeries, all three patients underwent DREZ microcoagulation to the spinal cord, caudal to the region of spinal cord transection at the injury site, to treat below-level pain. DREZ microcoagulation was guided by operative electrophysiological monitoring of the DREZ for electrical hyperactivity.

Pain was experienced continuously in all three patients with bursts in intensity occurring multiple times daily. Pain was exacerbated by any noxious stimulus to the body such as a skin sore, or urinary tract infection. Pain occurred in regions of the body in which sensation was absent to testing. All three patients rated their pain as a 10 on a scale of 1 to 10, 10 considered near suicidal-level pain.

All patients underwent preoperative plain radiography, CT scanning, and MR imaging to evaluate the spine and spinal cord. Any patient with suicidal ideation underwent preoperative psychological evaluation and received clearance. Preoperatively all patients had undergone extensive pharmacological treatment including administration of oral antidepressant, anti-seizure, and narcotic medications. In general, these medications were considered ineffective, although "took the edge off" in one patient.

Methods of DREZ recording were described in a previous publication and were used in this study (Falci S, Best L, Bayles R, Lammertse D, Stames C. J Neurosurg Spine 97:193-2000, 2002, incorporated by reference herein in its entirety.) Multilevel laminectomies were performed to expose the spinal cord at the injury site and level of spinal cord transection, as well as all spinal cord regions more caudal, to the level of the conus medullaris. Seven to eight laminectomies were performed in each of the three patients. Spinal levels were determined by intraoperative radiology evaluation or knowledge of levels of existing spinal instrumentation. Intraoperative ultrasonography was used to identify the level of spinal cord injury and region of spinal cord transection. The dura mater was opened and the DREZs identified using microscopic technique. Electrophysiological analyses of the DREZs were then performed from the injury site to the tip of the conus medullaris. To conduct such analyses, an active electrode was inserted into the specific DREZ. The active electrode was a 25-mm monopolar electrode (model MF 25; TECA Corporation, Pleasantville, N.Y.) with the distal 2 mm exposed. The electrode was implanted "free hand" in the DREZ with use of the intraoperative microscope to a 2 mm depth. The axis of implantation was approximately 35 to 45 degrees medially and was the same axis used for DREZ microcoagulation. Ground and reference Grass subdermal electroencephalographic electrodes were placed in exposed paraspinous muscle bilaterally. Spontaneous electrophysiological recordings were obtained using an evoked potential averager (Cascade Pro 32 Channel; Cadwell Laboratories, Kennewick, Wash.) at a gain setting of 50 with the high-frequency filter set at 3 kHz and the low-frequency filter set at 100 Hz. The recordings were one second in duration.

Figure 3:
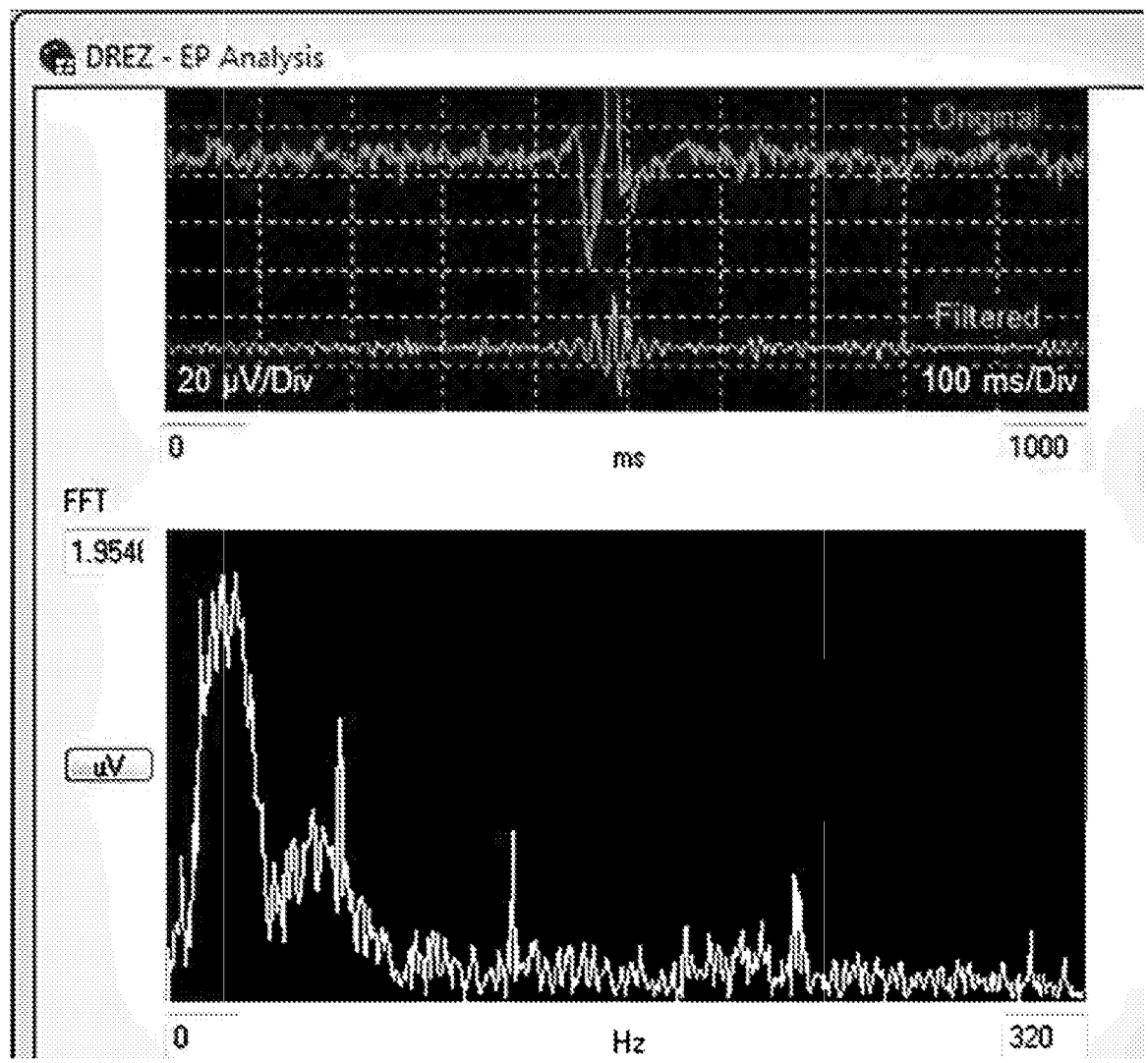
FIG. 3 depicts normal DREZ recording unfiltered, filtered data (spindles) and FFT labeled data, according to an illustrative embodiment.
Figure 4:
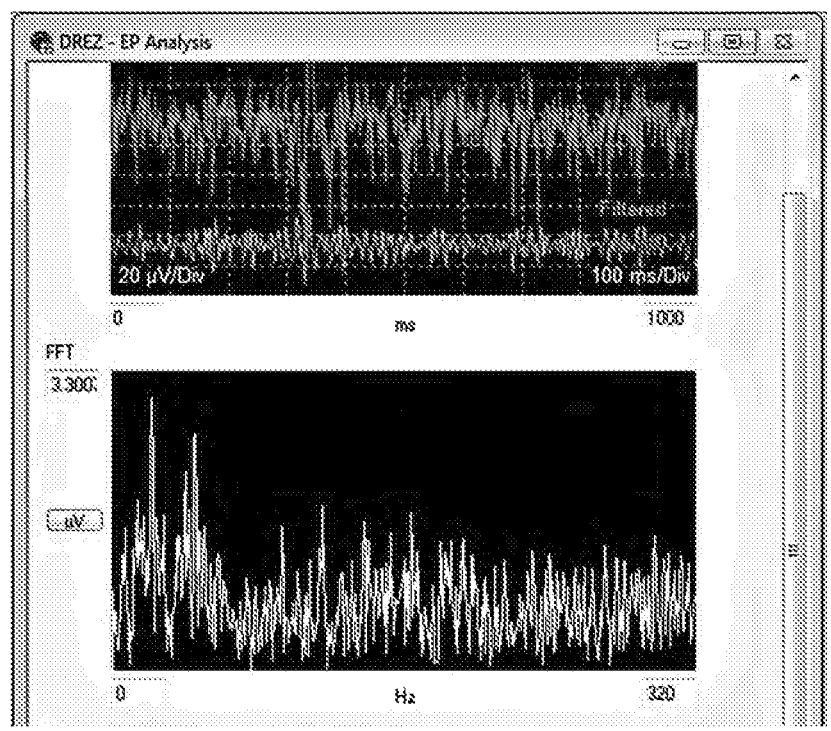
FIG. 4 depicts electrically hyperactive DREZ recording showing an increase in peak-to-peak voltage of original recording, increase in spindles, and skewing of high electrical activity across frequency spectrum compared to FIG. 3, according to an illustrative embodiment.
Figure 5:
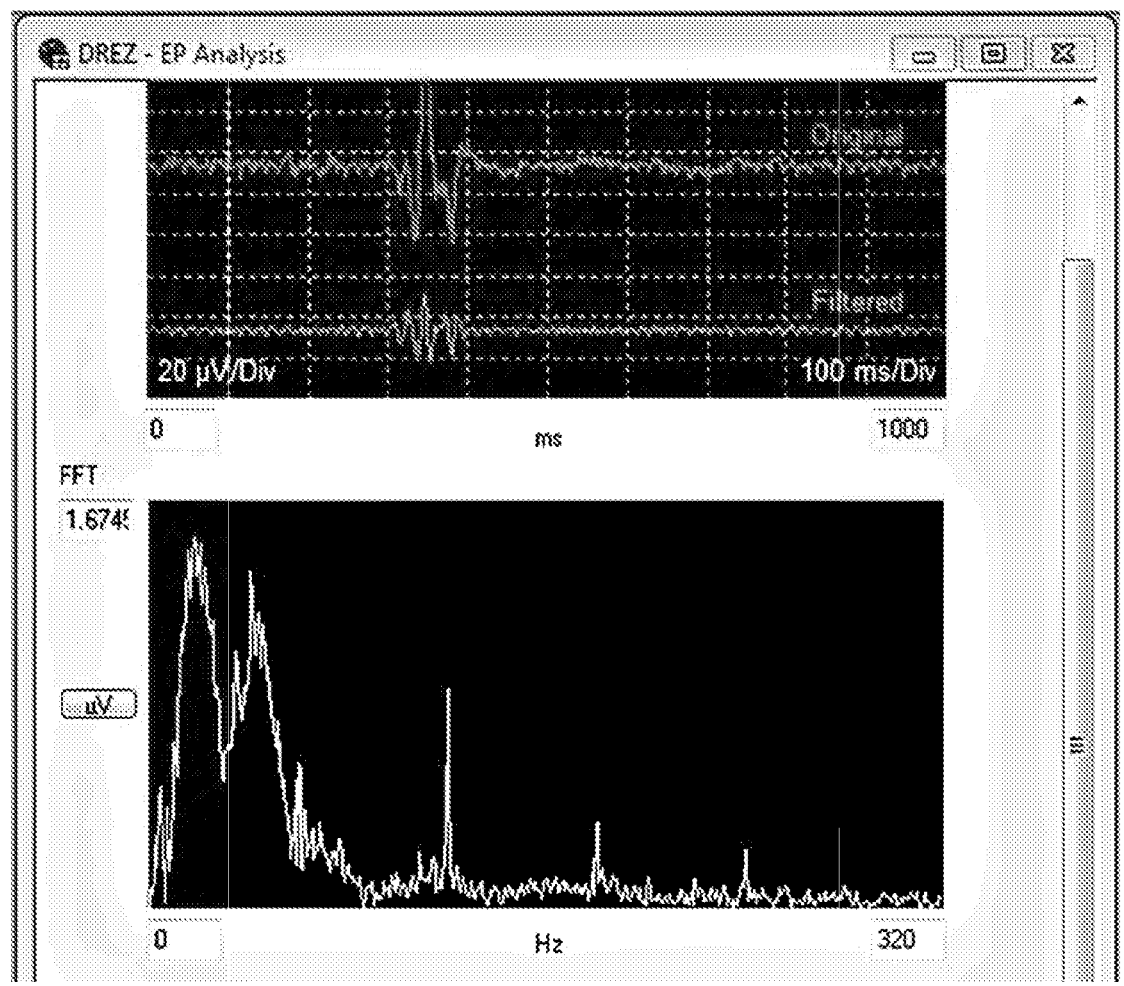
FIG. 5 depicts a post-microcoagulation DREZ recording of a patient in which the frequency plot is skewed toward lower frequencies and absence of spindles compared to FIG. 4, according an illustrative embodiment.

Methods of data analysis were described in a previous publication and were used in this study. (Falci S, Best L, Bayles R, Lammertse D, Stames C. J Neurosurg Spine 97:193-2000, 2002, incorporated by reference herein in its entirety.) In brief, the initial data were analyzed by RMS (expressed in microvolts), frequency and voltage in the waveform by FFT, and area under the waveform curve (expressed in microvolts per millisecond). These same analyses were performed to test data subsequent to DREZ microcoagulation. Both RMS analysis and area-under-the-waveform data provided a single numerical value of the recorded neuro-electrical energy. Analyses were performed using a subroutine in the Cadwell Cascade software. A phenomenon that we describe as "spindles" was examined by passing the initial data through a tight digital filter with a band pass of 65 to 100 Hz. A visual count was made of the number of spindle bursts in the 1-second recording, excluding artifacts caused by cardiac electrical activity or electrode movement. With these analyses, two distinct electrophysiological DREZ activities were found, consistent with our previous study. Those activities showing lower voltage and frequencies, smaller area under the waveform curve, and fewer than three spindles were considered to be non-pain-producing DREZ activity (FIG. 3) those showing higher voltage and frequencies, greater area under the waveform curve, and more than 3 spindles were considered to be regions of abnormal pain-producing neuro-electrical hyperactivity (FIG. 4). Analyses were also performed subsequent to DREZ microcoagulation of regions of abnormal neuro-electrical hyperactivity. It is notable that values of diminished activity are even less than those consistent with non-pain-producing activity (FIG. 5).

DREZ microcoagulation was performed using a needle tipped electrocautery (Covidien Force FX electrosurgical generator, Valleylab, Inc, Boulder, Colo.) at a setting of 10 desiccate for a one second pulse, with 1 mm of separation in all DREZs in which spontaneous neuro-electrical hyperactivity was demonstrated. Following microcoagulation, neuro-electrical hyperactivity was again measured. If recorded traces showed absence of neuro-electrical hyperactivity, no further lesions were made. If however, recorded traces continued to show spontaneous neuro-electrical hyperactivity, microlesioning was repeated.

Figure 7:
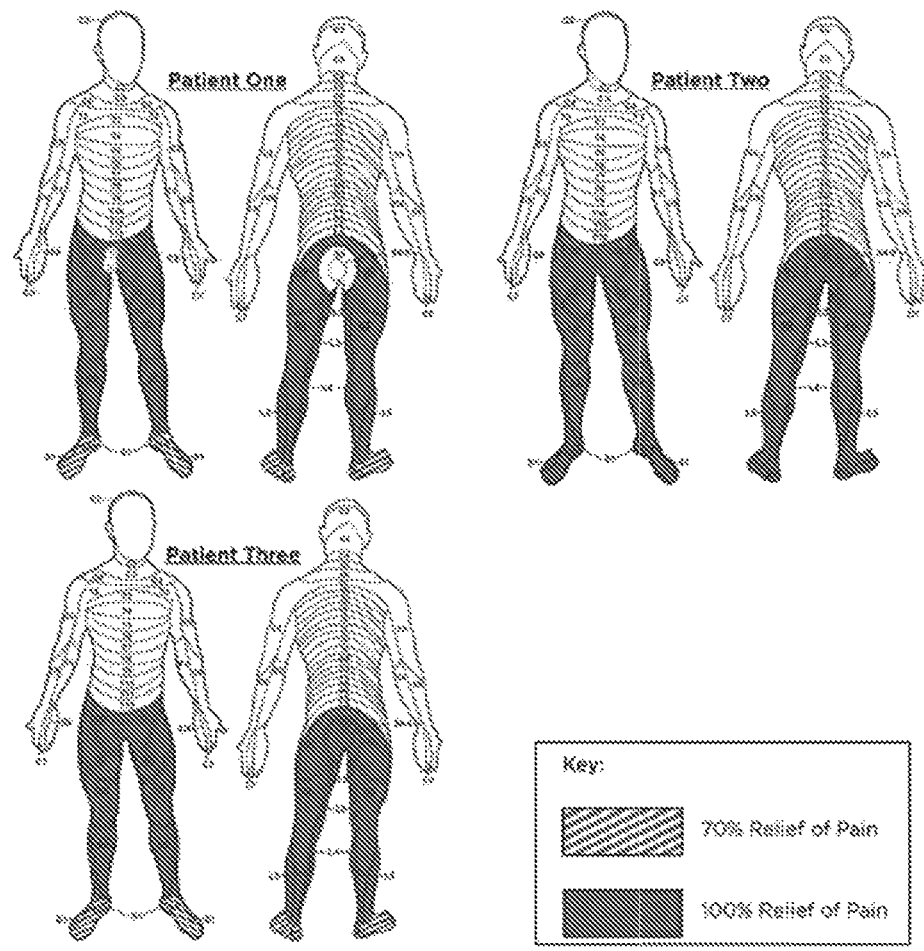
FIG. 7 depicts postoperative regions of pain relief in patients, according to an illustrative embodiment.

Complete or near complete relief of all below-level neuropathic pains were achieved in all three patients. 100% pain relief was reported in gluteal, rectal, genitalia, upper leg, and lower leg and feet in all three patients, with the exception of residual burning and electrical sensations in the feet in one patient, rated 0-3 out of 10 in intensity, and a non-painful "tingling" and "warmth" sensation in the feet of another rated 0-3 out of 10 in intensity (FIG. 7). Two of the three patients were able to completely wean off of all their preoperative pain medications which included Duragesic patch, Neurontin, and Cymbalta. Follow-up examination was performed 1%, 2% and 11 years respectively in the three patients. Follow-up observation regarding pain relief was accomplished by telephone interview and outpatient evaluation. Pain evaluation was a verbal scale in which scores of 1-10 indicated intensity of pain.

All three patients underwent preoperative and postoperative ASIA sensory and motor testing. There were no changes in testing as anticipated in these ASIA A patients with surgery only caudal to the injury site. There were no cases of wound infection, deep venous thrombosis, pulmonary embolus, cerebrospinal fluid leakage, or death. One patient developed a postoperative pseudomeningocele which resolved non-surgically within six months postoperatively.

At 10 months postoperatively, the same patient developed urosepsis with disc space infection and instability at L1/2 requiring surgical stabilization. At 3 years postoperatively, the same patient developed urosepsis with epidural abscess formation and instability at T12/L1, once again requiring stabilization. These episodes of instability were not considered treatment-related. Reported pain reduction remained subsequent to these two surgeries.

DREZ hyperactivity in T3-T7 spinal cord regions will result in truncal below-level central pain, hyperactivity in T8-T10 spinal cord regions, gluteal, rectal, and/or genitalia region below-level pains, and hyperactivity in T11-L1 DREZs upper, lower leg, and foot below-level pain. All three patients in this study experienced upper leg, lower leg, and foot below-level pains. All three patients additionally had DREZ hyperactivity recorded in more traditional DREZs of sensory rootlets subtending classical somatic pain for these same body regions (i.e. L1-S1) (Table 2).

TABLE 2

| | Patient | | |
|---|---|---|---|
| Levels of operative DREZ hyperactivity | 1 | 2 | 3 |
| T10 | | X | X |
| T11 | X | X | X |
| T12 | X | X | X |
| L1 | X | X | X |
| L2 | X | X | X |
| L3 | X | X | X |
| L4 | X | X | X |
| L5 | X | X | X |
| S1 | X | X | X |
| S2 | X | X | X |

Two of the three patients experienced below-level gluteal, rectal, and genitalia region pains and both had DREZ hyperactivity recorded in T10 DREZs. Both additionally had DREZ electrical hyperactivity recorded in the more traditional DREZ of sensory rootlets subtending classical somatic pain from these regions (i.e. S2) (Table 2).

Figure 8:
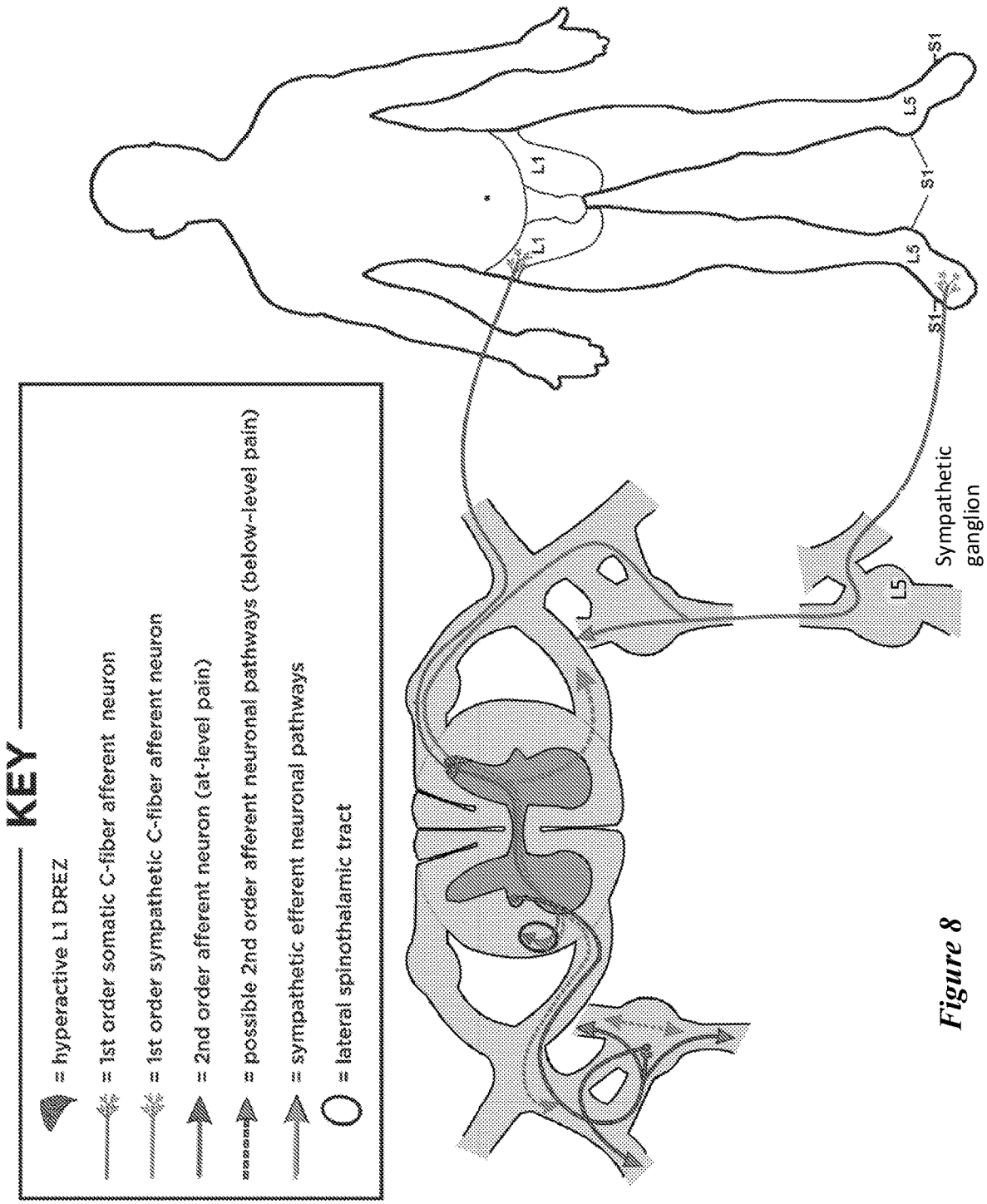
FIG. 8 depicts a cross section represents the L1 spinal cord at or immediately cephalad to the level of SCI, of a patient with both at-level inguinal region and below-level foot pain and DREZ hyperactivity solely at L1 (cross-hatch), according to an illustrative embodiment.

Spinal cord caudal to the level of a completely transected spinal cord (the neurological injury) can be a source of below-level spinal cord injury neuropathic pain, and with regard to the patients in this example, essentially a sole source. Further, below-level SCI neuropathic pain transmission can be substantially through the sympathetic chain and SNS-mediated pain pathways. To reach supraspinal pain centers, a new neuronal circuit must form post-injury, perhaps through reactive C-fiber sprouting, between hyperactive DREZs caudal to the level of spinal cord transection, and the sympathetic chain and spinal cord regions more cephalad to the transection, and/or the brain directly through the sympathetic chain and then occipital foramen. Transmission of DREZ hyperactivity through this new circuit may occur through ventral roots to the sympathetic chain, or in a retrograde fashion through dorsal roots to the sympathetic chain, with re-entry into the spinal cord by way of ventral or dorsal roots (FIG. 8). At-level somatic C-fiber afferents coursing from the inguinal region and below-level sympathetic C-fiber afferents coursing from the foot are shown converging on the same L1 DREZ. The proposed second-order sympathetic afferent pathways are similar to sympathetic efferent pathways. Transection of the spinal cord cephalad to the L1 level could arrest at-level pain transmission to the supraspinal centers, but not below-level pain transmission. Additional support of this proposed mechanism is the historical failure of cordectomy and cordotomy to relieve below-level SCI neuropathic pain, as well as our own personal experience with cordectomy.

Example 4

Figure 9:
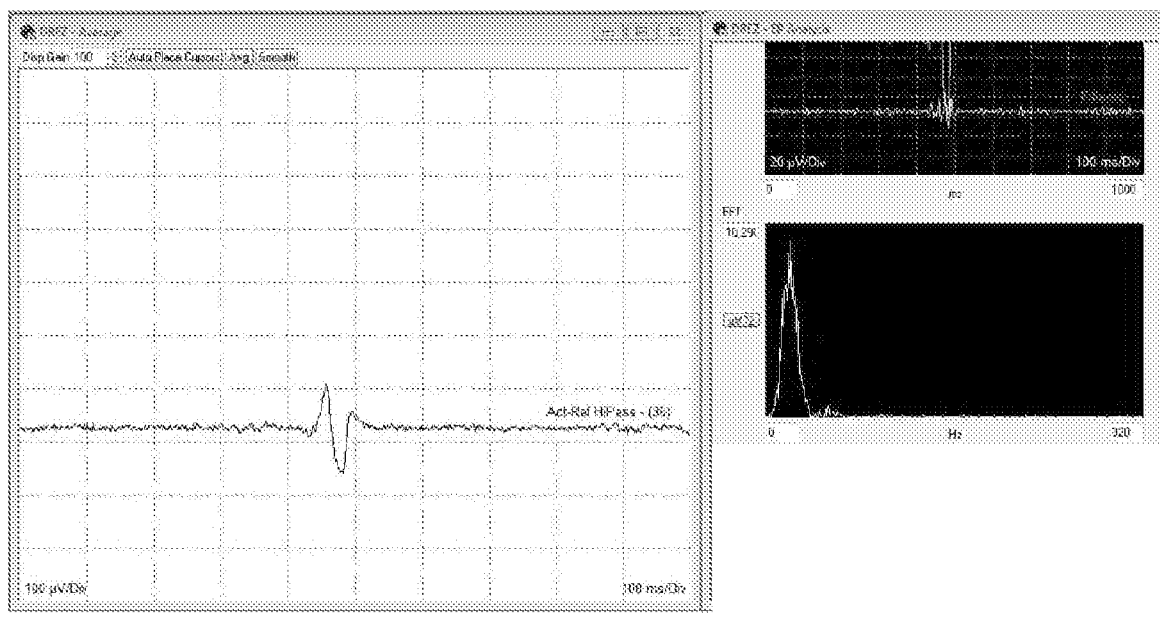
FIG. 9 depicts normal electrical activity of the DREZ of T10 in regions below the cervical level of SCI in a complete quadriplegic patient with leg pain, according an illustrative embodiment.
Figure 10:
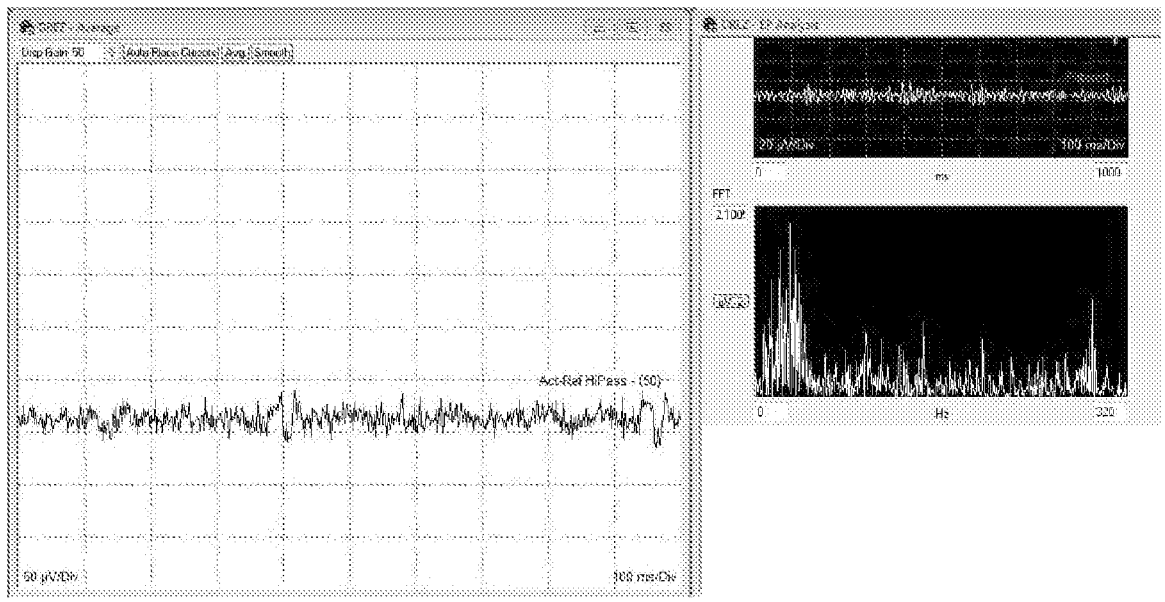
FIG. 10 depicts electrical hyperactivity in the DREZ of T11 below the cervical level of complete spinal cord injury, according an illustrative embodiment.

FIG. 9 shows normal electrical activity of the spinal cord DREZ of T10 in regions below the cervical level of SCI in a complete quadriplegic with leg pain. FIG. 10 shows electrical hyperactivity in the DREZ of T11 below the cervical level of complete spinal cord injury corresponding to a somatotopic map of leg DREZ pain generating tissue in cord regions. That the DREZ pain generator is located caudal to the cervical level of complete SCI and that SCI neuropathic pain is perceived below the level of complete SCI shows that the central neuropathic pain is sympathetically mediated. The presence of pain perceived by the patient to be below the level of spinal cord injury shows that pain is below the level of sympathetically mediated pain.

Having described several embodiments, it will be recognized by those skilled in the art that various modifications, alternative constructions, and equivalents may be used without departing from the spirit of the disclosure. Additionally, a number of well-known processes and elements have not been described in order to avoid unnecessarily obscuring the disclosure. Accordingly, the above description should not be taken as limiting the scope of the disclosure.

Those skilled in the art will appreciate that the disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the method and system, which, as a matter of language, might be said to fall there-between.

The invention claimed is:

1. A method of treating neuropathic pain in a spinal cord injured individual in need thereof, comprising administering 2-(2-oxo-4-propylpyrrolidin-1-yl)butanamide to the individual,
   wherein the pain is generated by spinal cord tissue caudal to the level of the spinal cord injury, and
   wherein the neuropathic pain is sympathetically mediated spinal cord injury pain perceived by the patient to be below the level of spinal cord injury.

2. The method of claim 1, wherein the 2-(2-oxo-4-propylpyrrolidin-1-yl)butanamide is administered intrathecally below the level of the spinal cord injury.

* * * * *